United States Patent [19]

Thomas et al.

[11] Patent Number: 5,624,849
[45] Date of Patent: Apr. 29, 1997

[54] METHOD AND APPARATUS FOR FILLING GLASS CAPILLARY TUBES

[75] Inventors: Bradley S. Thomas, Timonium; Mark L. Sussman, Baltimore, both of Md.

[73] Assignee: Becton Dickinson and Company, Franklin Lakes, N.J.

[21] Appl. No.: 520,998

[22] Filed: Aug. 30, 1995

[51] Int. Cl.$^6$ ............................... G01N 1/10; B01L 3/02
[52] U.S. Cl. .................. 436/180; 422/99; 422/100; 73/864.01; 73/864.74; 128/763; 128/765; 141/329; 141/330
[58] Field of Search .............................. 422/99, 100, 102, 422/104, 103; 141/329, 330; 73/864.01, 864.02, 864.74; 436/180; 128/763, 765

[56] References Cited

U.S. PATENT DOCUMENTS

| | | | |
|---|---|---|---|
| 3,987,791 | 10/1976 | Chittenden et al. | 128/272.3 |
| 4,886,072 | 12/1989 | Percarpio et al. | 128/763 |
| 4,972,843 | 11/1990 | Broden | 128/760 |
| 5,065,768 | 11/1991 | Colmen et al. | 128/760 |
| 5,112,327 | 5/1992 | Linuma et al. | 604/413 |
| 5,151,184 | 9/1992 | Ferkany | 210/514 |
| 5,270,219 | 12/1993 | DeCastro et al. | 436/180 |
| 5,286,453 | 2/1994 | Pope | 422/100 |
| 5,413,246 | 5/1995 | Godolphin et al. | 222/1 |
| 5,454,409 | 10/1995 | McAffer et al. | 141/329 |
| 5,460,782 | 10/1995 | Coleman et al. | 422/100 |

Primary Examiner—Harold Pyon
Attorney, Agent, or Firm—Bruce S. Weintraub

[57] ABSTRACT

The present invention relates to a method and apparatus for transferring fluid from a blood collection tube to a glass capillary tube. This eliminates the need for health care workers to open the blood collection tube, insert a glass capillary tube into the blood collection robe, pipet a fluid such as blood into the tube and be exposed to the excess fluid from the capillary tube. The apparatus of the present invention is directed to a transfer device, and a dispenser which can be used with the transfer device, for carrying out this method.

8 Claims, 3 Drawing Sheets

METHOD AND APPARATUS FOR FILLING GLASS CAPILLARY TUBES

FIELD OF THE INVENTION

The present invention relates to a method and apparatus for transferring fluid to glass capillary tubes from blood collection tubes. The present invention eliminates the need for opening the blood collection tube, inserting a capillary tube into the blood collection tube, pipetting the blood, and having to wipe the excess fluid from the capillary tube. The apparatus of the present invention is directed to an improved device and a dispenser for carrying out this method.

BACKGROUND OF THE INVENTION

U.S. Pat. Nos. 4,027,660 issued Jun. 7, 1977; and 4,082,085 issued Apr. 4, 1978 relate to a technique for performing differential leukocyte counts in a sample of anticoagulated whole blood which has been drawn into a capillary tube and centrifuged. A generally cylindrical float is disposed in the capillary tube in the blood sample during centrifugation. The float settles into the erythrocyte layer and extends through the buffy coat so as to physically elongate the leukocyte and platelet layers. A stain such as acridine orange is used to differentially color the different constituents which make up the buffy coat so that the buffy coat appears as a plurality of differently colored bands in the capillary tube (typically a glass capillary tube which is also called a Quantitative Buffy Coat or QBC tube). The layering of the constituents according to density during centrifugation allows cell counts to be made by measuring the distance between the boundaries of each cell band.

It is highly desirable to transfer a fluid (such as blood) into and fill a glass capillary tube such as that utilized in the above technique without opening a blood collection tube. It is desirable to limit the exposure of, for example, health care workers of any kind, to possible blood-borne pathogens to whatever extent is technologically possible. The use of cap-piercers with impedance style hematology analyzers has now become commonplace.

One device which is presently available and addresses these concerns is called Diff-Safe™ Blood Dispenser (Patent Pending). This device is manufactured for Alpha Scientific Corporation, P.O. Box 617, Wayne, Penn. 19807-0617. The purpose of the device is to allow a drop of blood from an EDTA tube to be placed on a slide to prepare a differential smear without opening the blood tube. The device is a simple molded plastic part with a blunt cannula which pierces the EDTA blood tube closure. When the user presses the device against the slide a positive pressure is exerted inside the blood tube by a slight displacement of the elastomeric closure. This positive pressure forces a drop of blood out the cannula which is deposited on the slide The present invention describes an improvement over this device which allows safe and effective transfer of a fluid such as blood from a blood collection tube into a glass capillary tube, without any spillage or danger of exposure. Such filling of a glass capillary tube can enable one to utilize these filled glass capillary tubes in, for example, the above-described QBC technique.

SUMMARY OF THE INVENTION

The present invention relates to a method and apparatus (including a device and dispenser) for transferring fluid from a blood collection tube to a glass capillary tube. The device is a transfer device having a distal end with a channel capable of receiving a glass capillary tube, and a proximal end with a chamber capable of receiving a blood collection tube with an elastomeric closure. There is a cannula which is mounted at the proximal end of the transfer device which can pierce the closure in the blood collection tube and a fluid pathway which allows fluid to flow through the cannula into the glass capillary tube from the blood collection tube thus allowing safe transfer of blood without any spillage.

The dispenser has means for holding the transfer device, an area for receiving the blood collection tube and the glass capillary tube, a pusher mechanism directly above the bottom of the blood collection tube and a handle which activates the pusher mechanism for dispensing the blood from the blood collection tube into the glass capillary tube. The handle of the dispenser is located parallel to the means for holding the transfer device

DETAILED DESCRIPTION OF THE INVENTION

The present invention is directed to a method and apparatus for transferring fluid to a glass capillary tube from a blood collection tube. In one embodiment, the apparatus of the present invention is a transfer device.

Figure 1A:
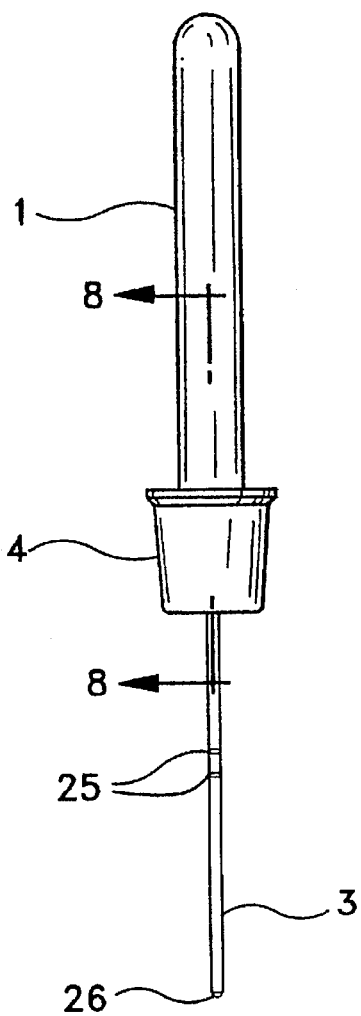
FIG. 1a shows a transfer device according to the present invention.
Figure 1B:
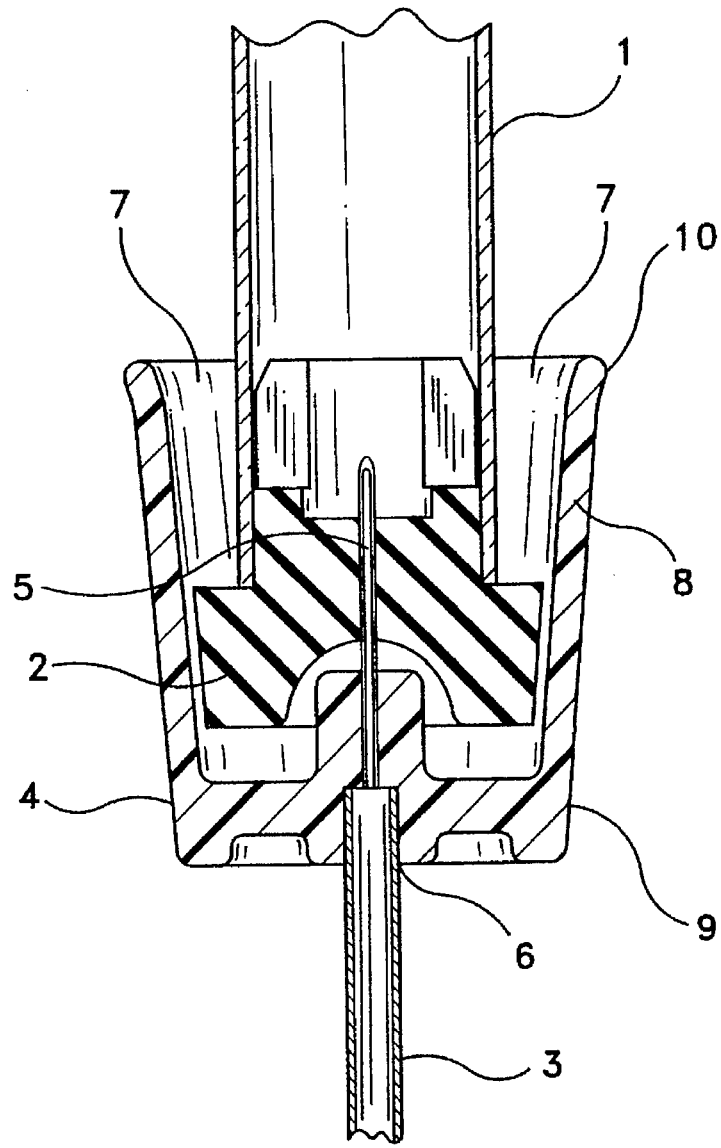
FIG. 1b shows a cutaway side view of this device along Section B—B.

The transfer device of the present invention, which is capable of transferring fluid from a blood collection tube to a glass capillary, tube, and is demonstrated in FIG. 1a and 1b, comprises:

a channel (6) for receiving a glass capillary tube (3) at the distal end (9) of the transfer device (4);

a chamber (7) at the proximal end (10) of the transfer device (4) for receiving the blood collection tube (1) having an elastomeric closure (2);

a cannula (5) mounted within the transfer device (4) at the proximal end (10) of the device;

a fluid pathway in the transfer device (4) from the blood collection tube (1) to the glass capillary tube (3).

As shown in FIG. 1b, the transfer device has a cannula (5). This cannula (5) is capable of piercing the elastomeric closure (2) of the blood collection tube (1). The glass capillary tube (3) can be inserted into the channel (6) in the distal end (9) of the transfer device (4). When inserted into this channel (6), the capillary tube (3) will have a somewhat snug fit, so that blood will not leak around the channel (6), but can be loose enough to allow easy insertion and removal of the tube (3).

In a further preferred embodiment, as shown in FIG. 1b, the chamber (7) at the proximal end (10) of the transfer device (4) has a skin (8) extending from the proximal end (10) which surrounds the chamber (7). This skin (8) can surround the top of the blood collection tube (1) having the elastomeric closure (2).

In yet another preferred embodiment, the following method can be used to transfer a fluid, and preferably blood, from the blood collection tube (1) to the capillary tube (3).

The chamber (7) with a skin (8) at the proximal end (10) of the transfer device (4) is first placed over the top of the blood collection tube (1) with the cannula (5) piercing the closure (2). The capillary tube (3) is gently inserted into the channel (6) at the distal end (9) of the device (4). The assembly is tilted so that the distal end (6) is below the proximal end (10), so that the fluid flows from the bottom of the blood collection tube (1) into the closure (2). Holding both the collection tube (1) and the transfer device (4) in one hand, pressure is applied on the transfer device (4) in the direction of the blood collection tube (1) to displace the elastomeric closure (2); thus causing fluid to flow through the cannula (5) into the glass capillary (QBC) tube (3). The pressure is continued to be applied until the glass capillary tube (3) contains sufficient volume of fluid which has flowed through the cannula (5) into the glass capillary tube (3) as indicated by fill lines (25) on the capillary tube (3). The capillary tube (3) is then removed from the device (4), and the pressure on the transfer device (4) is released The above preferred method provides a safe and acceptable mode for transferring fluid from a blood collection tube to a glass capillary tube without opening the blood collection tube.

However, for users with small hands or limited hand strength, this method may prove to be somewhat difficult to facilitate. Thus, also disclosed herein in a preferred embodiment is a dispenser, for use together with the transfer device, which would be highly desirable for these users. Such a dispenser is capable of reproducibly exerting the correct amount of displacement of the transfer device on the elastomeric closure necessary to fill the capillary tube to the desired volume.

The dispenser of the present invention can preferably have the following characteristics:

a) The ability to handle several different sizes of blood collection tubes ranging in volume from about 3 ml. to about 20 ml.

b) The ability to have a preset volume displacement to reproducibly dispense the proper amount of blood.

c) The ability to vary the preset volume to transfer fluid from blood collection tubes to capillary tubes and fill several different capillary tubes. A preferred range would be from about 50 µl to about 150 µl;

d) A mechanism for one way filling, so no back flushing with blood is possible. This mechanism may be a ratchet mechanism in the dispense handle, or a one way valve in the transfer cap, or any other similar mechanism to provide one way flow.

In a preferred embodiment, the dispenser of the present invention has a means for holding the transfer device; an area for receiving the blood collection tube; an area for receiving the glass capillary tube; a pusher mechanism located directly above the area for receiving the bottom of the blood collection tube; and a handle for dispensing the fluid from the blood collection tube into the glass capillary tube through the transfer device by activating the pusher mechanism.

Figure 2:
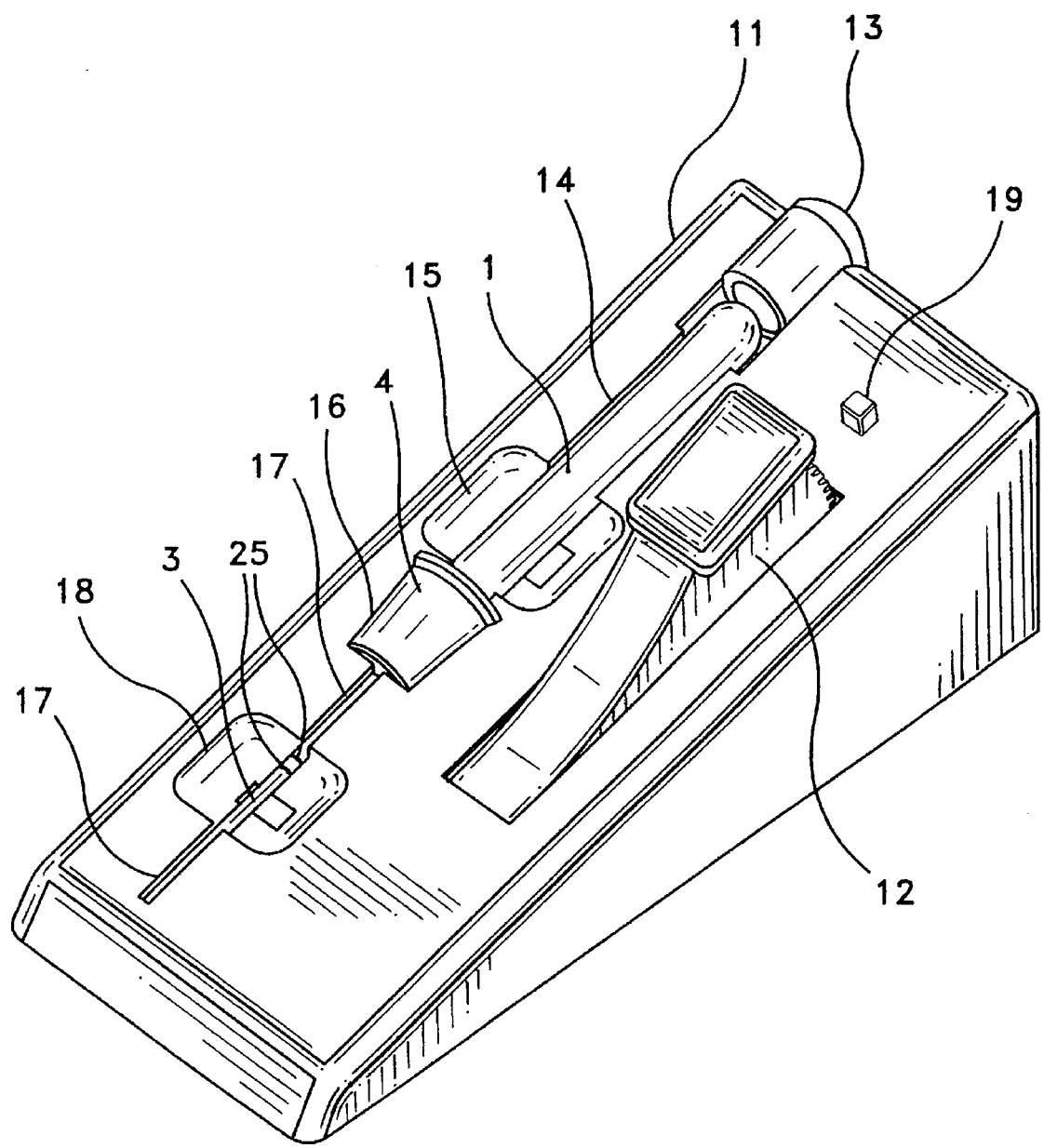
FIG. 2 shows an isometric view of a dispenser holding a blood collection tube, transfer device and glass capillary tube.
Figure 3A:
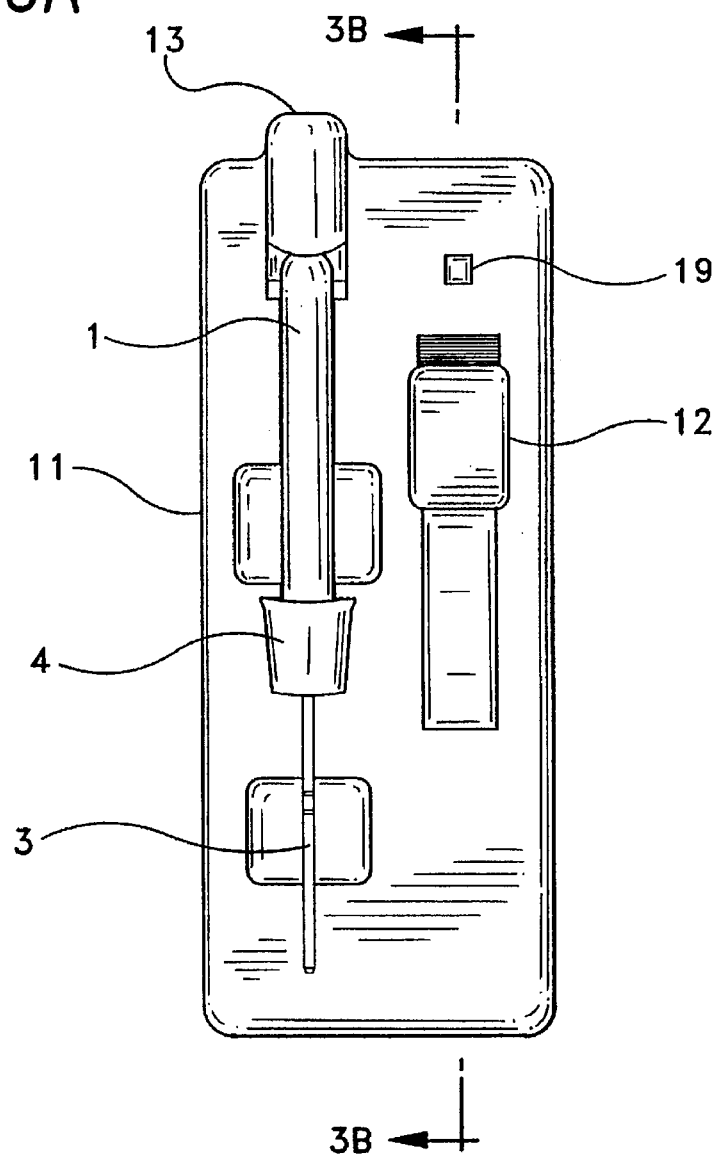
FIG. 3a shows a top planar view of the dispenser in FIG. 2.
Figure 3B:
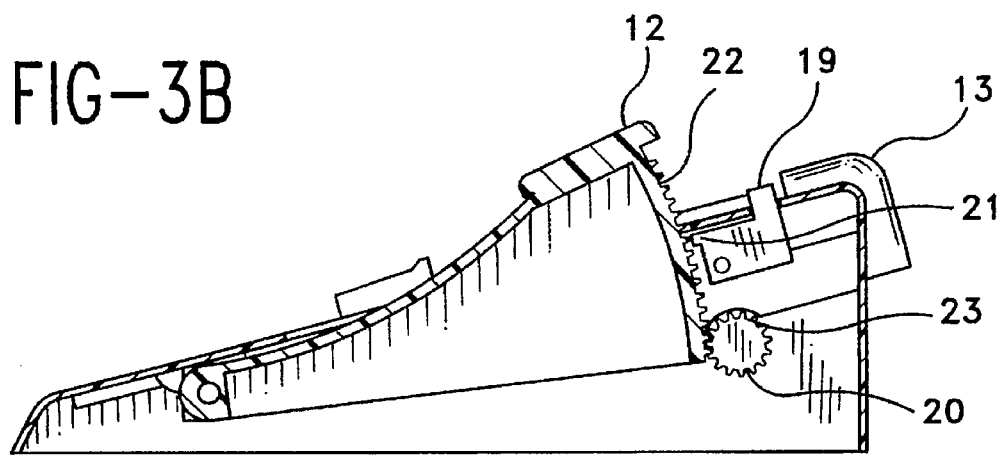
FIG. 3b shows a cut-away side view of this dispenser along Section A—A.

A dispenser of the type described above is demonstrated in FIG. 2 and FIG. 3a and 3b. The handle (12) is located parallel to the means for receiving the transfer device in these figures. However, it is not required that the handle must be juxtaposed in this manner for all embodiments of the dispenser. FIG. 2, FIG. 3a and 3b merely demonstrate one embodiment of the invention.

The handle of the dispenser is connected to the pusher mechanism by a mechanism which causes the forward motion of the pusher mechanism; pressing the cannula in the transfer device into the elastomeric closure. A mechanical stop can be provided to assure the correct displacement. Also, the handle can be ratcheted to prevent back flushing of the blood.

In another preferred embodiment, the dispenser as shown in FIG. 2, 3a and 3b can be utilized in the following method, which is capable of using either embodiment of the transfer device disclosed herein.

The transfer device (4) is placed over the top of the blood collection tube (1) having an elastomeric closure with the cannula piercing the closure (not shown). The transfer device (4) with the blood collection tube (1) is then placed in the grooves (14, 15, 16) in the dispenser (11). The capillary tube (3) is inserted into channel (6) in the transfer device (4) and rests in an area (17, 18) in the dispenser (11) for receiving the capillary tube. The user displaces the handle (12) sufficiently to activate the pusher mechanism (13) to provide the appropriate displacement on the blood collection tube (1), producing a positive pressure to dispense the appropriate volume of fluid which can be from about 50 µl to about 150 µl, into the capillary, tube (3). The user can then remove the capillary tube (3) from the transfer device (4). The user can then, if desired, manually mix and seal the capillary tube (3) at the closure (26). The closure (26) can be seen in FIG. 1a. The user releases the ratchet on the handle (12). The ratchet release can be a release button or bar alongside, next to, or above the handle (12). In FIG. 2, 3a and 3b the release button (19) is above the handle. The user can then remove the transfer device (4) and blood collection tube (1) from the dispenser. The transfer device (4) and blood collection tube (1) may be left attached together for later disposal.

The ratchet referred to above functions to prevent the device from pulling blood back into the blood collection tube (1) after the capillary tube (3) is filled. In use, the user places the blood collection tube (1) with the transfer device (4) piercing the elastomeric closure into the dispenser (11). The user then places a capillary tube (3) into grooves (17) in the dispenser with its open end entering the channel (6) in the transfer device (4). When the handle (12) is depressed, the pusher mechanism (13) of the dispenser (11) pushes the blood collection tube (2) against the transfer device (4) forcing blood out through the cannula and into the capillary tube (3) which is filled by capillary action, as indicated by fill lines (25) on the capillary tube (3). Without the presence of the ratchet, which is an optional feature of the present invention, the user would have to hold the exact lever position where the blood is between the capillary tube fill lines while removing the capillary tube. When the pressure on the handle was relaxed, the pressure would drop inside the blood collection tube and draw some of the blood back from the capillary tube Thus as shown in FIG. 3b, the downward movement of the handle (12) causes the handle teeth (22) to rotate a pinion gear (20) which in turn engages the rack teeth (23) under the tube pusher (13). This causes the tube pusher (13) to move forward in proportion to the downward motion of the handle (12). By adjusting the two pitch diameters of the pinion engaging the handle and the pusher, the ratio between downward motion of the handle and forward motion of the pusher can be adjusted. The handle (12) is spring loaded upward to return the handle (12) and pusher (13) to their home position after use. The ratchet is a simple spring loaded pawl (21) that engages the handle teeth (22) in the handle (12). The pawl is biased towards the handle teeth. The ratchet is pushed out of the way during downward motion, but catches the handle teeth (22) if the motion reverses. This retains the handle (12) in the position where the user has stopped until the user presses the release button (19) on the pawl (21) which rotates it free of the handle teeth (22) and allows the handle (12) to spring back up. With this system, the user presses the handle (12) until the user sees that the blood is between the fill lines in the capillary tube, stops and removes the QBC tube, then presses the release button (19) to free the blood collection tube for removal.

The present method, transfer device and dispenser eliminate the need to open blood collection tubes or to immerse capillary tubes in a fluid such as blood, thus avoiding an undesirable wiping step The method, device and the dispenser described therefore provides considerable safety advantages to users of for example, QBC brand venous blood analysis tubes.

We claim:

1. A method for transferring fluid from a blood collection tube to a glass capillary tube comprising:

providing an apparatus consisting of a transfer device and a dispenser, said transfer device having a distal end with a channel capable of receiving a glass capillary tube, a proximal end with a chamber capable of receiving a blood collection tube with an elastomeric closure, and a cannula mounted at the proximal end of the transfer device, and said dispenser having a means for holding the transfer device, an area for receiving the blood collection tube, an area for receiving the glass capillary tube, a pusher mechanism capable of pushing the blood collection tube into the transfer device, and a handle capable of activating the pusher mechanism;

placing the transfer device with the cannula over the top of the blood collection tube having an elastomeric closure;

piercing the closure with cannula;

placing the transfer device and blood collection tube into the dispenser;

inserting a glass capillary tube into the transfer device and allowing the glass capillary tube to rest in the area for receiving said capillary tube;

displacing the handle on the dispenser in order to activate the pusher mechanism and dispense an appropriate volume of fluid into the glass capillary tube; and removing the capillary tube from the transfer device.

2. The method of claim 1 wherein the appropriate volume of fluid to be dispensed into the glass capillary tube is from about 50 µl to about 150 µl.

3. The method of claim 1 wherein the area for receiving the blood collection tube can receive a tube ranging in volume from about 3 ml to about 20 ml.

4. An apparatus for transferring fluid from a blood collection tube to a glass capillary tube comprising:

a transfer device having a distal end, a proximal end, and a fluid pathway extending between the distal end and the proximal end;

a channel for receiving a glass capillary tube at the distal end of the transfer device;

a chamber extending from the proximal end of the transfer device for receiving a blood collection tube having an elastomeric closure;

a cannula extending from the proximal end of said transfer device for piercing the closure on the blood collection tube and permitting fluid in the blood collection tube to pass into the capillary tube; and a dispenser having,
      means for holding the transfer device;
      an area for receiving the blood collection tube;
      an area for receiving the glass capillary tube;
      a pusher mechanism located directly above the area for receiving the blood collection tube; and
      a handle for dispensing the fluid from the blood collection tube into the glass capillary tube through the transfer device by activating the pusher mechanism.

5. The apparatus of claim 4 further comprising a skin extending from the proximal end of said transfer device and surrounding the chamber.

6. The apparatus of claim 4 wherein the appropriate volume of fluid to be dispensed into the glass capillary tube is from about 50 µl to about 150 µl.

7. The apparatus of claim 4 wherein the area for receiving the blood collection tube can receive a tube ranging in volume from about 3 ml. to about 20 ml.

8. The apparatus of claim 5 wherein the area for receiving the blood collection tube can receive a tube ranging in volume from about 3 ml to about 20 ml.

\* \* \* \* \*

UNITED STATES PATENT AND TRADEMARK OFFICE
CERTIFICATE OF CORRECTION

PATENT NO. : 5,624,849
DATED : April 29, 1997
INVENTOR(S) : Bradley S. Thomas and Mark L. Sussman It is certified that error appears in the above-identified patent and that said Letters Patent is hereby corrected as shown below:

In Claim 5, Line 1, delete "skin" and substitute --skirt--.

Signed and Sealed this

Second Day of February, 1999

Attest:

Attesting Officer

*Acting Commissioner of Patents and Trademarks*